(12) United States Patent
Kraft et al.

(10) Patent No.: US 10,265,245 B2
(45) Date of Patent: Apr. 23, 2019

(54) PORTABLE DRUG DISPENSER

(76) Inventors: Daniel L. Kraft, Portola Valley, CA (US); Scott Parazynski, Houston, TX (US)

( * ) Notice: Subject to any disclaimer, the term of this patent is extended or adjusted under 35 U.S.C. 154(b) by 673 days.

(21) Appl. No.: 14/241,799

(22) PCT Filed: Aug. 27, 2012

(86) PCT No.: PCT/US2012/052551
§ 371 (c)(1),
(2), (4) Date: Jan. 4, 2016

(87) PCT Pub. No.: WO2013/033033
PCT Pub. Date: Mar. 7, 2013

(65) Prior Publication Data
US 2017/0326033 A1    Nov. 16, 2017

Related U.S. Application Data (60) Provisional application No. 61/528,225, filed on Aug. 27, 2011.

(51) Int. Cl.
G06F 19/00 (2018.01)
A61J 7/00 (2006.01)
A61J 7/04 (2006.01)

(52) U.S. Cl.
CPC .......... *A61J 7/0084* (2013.01); *A61J 7/0418* (2015.05); *A61J 7/0445* (2015.05); *A61J 7/0481* (2013.01); *G06F 19/00* (2013.01); *G06F 19/3462* (2013.01); *A61J 2200/30* (2013.01); *A61J 2205/70* (2013.01)

(58) Field of Classification Search
USPC ........................................................ 221/263
See application file for complete search history.

(56) References Cited

U.S. PATENT DOCUMENTS

| 4,983,401 A | 1/1991 | Eichel ........................... 424/473 |
| 5,699,649 A | 12/1997 | Abrams et al. ................. 53/428 |
| 5,941,380 A | 8/1999 | Rothman ..................... 206/222 |

(Continued)

FOREIGN PATENT DOCUMENTS

| JP | H05502529 | 4/1993 | ............. G06F 15/21 |
| JP | 2004534571 | 11/2004 | ................ A61J 7/00 |

(Continued)

OTHER PUBLICATIONS

EP Office Action and Supplemental European Search Report issued in corresponding European Patent Appln. No. 11817178.4, dated Nov. 7, 2016 (17 pgs).

(Continued)

*Primary Examiner* — Gene O Crawford
*Assistant Examiner* — Ayodeji T Ojofeitimi
(74) *Attorney, Agent, or Firm* — Hayes Soloway, P.C.

(57) ABSTRACT

A portable drug dispenser includes a chamber for holding a plurality of separately contained drug products, a dispensing mechanism for dispensing one or more of the plurality of drug products, and may optionally include a processor to determine the time of each activation of the dispensing mechanism and to transmit the determined time of activation to a computer located remote to the dispenser. The dispenser may include more than one chamber for holding drugs.

17 Claims, 2 Drawing Sheets

(56) References Cited

U.S. PATENT DOCUMENTS

| | | | | |
|---|---|---|---|---|
| 5,960,609 | A | 10/1999 | Abrams et al. | 53/428 |
| 6,428,809 | B1 | 8/2002 | Abrams et al. | 424/451 |
| 6,510,430 | B1 | 1/2003 | Oberwager | 128/921 |
| 6,564,121 | B1 | 5/2003 | Wallance et al. | 700/231 |
| 6,658,396 | B1 | 12/2003 | Tang et al. | 706/17 |
| 6,702,683 | B2 | 3/2004 | Abrams et al. | 464/465 |
| 6,923,979 | B2 | 8/2005 | Fotland et al. | 424/439 |
| 7,080,755 | B2* | 7/2006 | Handfield | A61J 7/0084 221/13 |
| 7,404,968 | B2 | 7/2008 | Abrams et al. | 424/443 |
| 8,116,907 | B2* | 2/2012 | Hyde | G06F 19/3462 700/236 |
| 8,518,022 | B2 | 8/2013 | Trovato et al. | 604/890.1 |
| 8,718,817 | B2 | 5/2014 | Hyde et al. | 700/231 |
| 2002/0042725 | A1 | 4/2002 | Mayaud | 705/2 |
| 2003/0010791 | A1 | 1/2003 | Gentiluomo | 221/92 |
| 2004/0158350 | A1 | 8/2004 | Ostergaard et al. | 700/231 |
| 2004/0172169 | A1 | 9/2004 | Wright | 700/265 |
| 2005/0086008 | A1 | 4/2005 | DiGianfilippo et al. | 702/19 |
| 2005/0150488 | A1 | 7/2005 | Dave | A61M 11/00 |
| 2005/0210834 | A1 | 9/2005 | Kamineni | 53/415 |
| 2006/0089856 | A1 | 4/2006 | Kadhiresan et al. | 705/2 |
| 2007/0016443 | A1 | 1/2007 | Wachman et al. | 705/2 |
| 2007/0087048 | A1 | 4/2007 | Abrams et al. | 424/451 |
| 2007/0122824 | A1 | 5/2007 | Tucker et al. | 435/6 |
| 2007/0186923 | A1* | 8/2007 | Poutiatine | A61J 7/0038 128/200.14 |
| 2008/0131362 | A1 | 6/2008 | Rousso et al. | 424/1.11 |
| 2008/0195249 | A1 | 8/2008 | Rousso et al. | 700/231 |
| 2009/0025741 | A1 | 1/2009 | Crawford et al. | 131/359 |
| 2009/0057328 | A1* | 3/2009 | Ratnakar | A61J 7/0481 221/1 |
| 2009/0105876 | A1 | 4/2009 | Simpson et al. | 700/242 |
| 2010/0100391 | A1 | 4/2010 | Daya et al. | 705/2 |
| 2010/0131097 | A1 | 5/2010 | Young et al. | 700/244 |
| 2010/0270257 | A1 | 10/2010 | Wachman et al. | 215/228 |
| 2010/0324728 | A1 | 12/2010 | Rosenblum | 700/242 |
| 2011/0146835 | A1 | 6/2011 | Terzini | 141/1 |
| 2012/0189693 | A1 | 7/2012 | Dick | 424/465 |
| 2012/0232473 | A1* | 9/2012 | Poutiatine | A61J 7/0053 604/60 |

FOREIGN PATENT DOCUMENTS

| | | | | |
|---|---|---|---|---|
| JP | 2005517504 | 6/2005 | | A61M 15/00 |
| JP | 2007522036 | 8/2007 | | B65D 51/28 |
| JP | 2008510558 | 4/2008 | | A61J 3/07 |
| JP | 2010-170504 | 8/2010 | | G06Q 50/00 |
| WO | WO 91/05310 | 4/1991 | | G06F 15/42 |
| WO | WO 99/61321 | 12/1999 | | |
| WO | WO 2002/069897 | 12/2002 | | |
| WO | WO2005073103 | 8/2005 | | B65D 51/28 |
| WO | WO 2006/028944 | 3/2006 | | G06F 17/00 |
| WO | WO2012021899 | 2/2012 | | G06Q 50/00 |

OTHER PUBLICATIONS

U.S. Office Action issued in U.S. Appl. No. 13/210,333 dated Dec. 7, 2016. (89 pages).

International Search Report and Written Opinion issued in corresponding PCT Patent Appln. Serial No. PCT/US12/52551 dated Nov. 2, 2012 (11 pgs).

Extended European Search Report issued in corresponding EPO Patent Appln. No. 12827879.3-1651, dated Apr. 21, 2015 (7 pgs).

Japanese Office Action issued in application No. 2013-524264, dated Feb. 29, 2016 (6 pgs).

Japanese Office Action issued in application No. 2014-528500, dated Apr. 13, 2016 (15 pgs).

Japanese Official Action issued in related Japanese Patent Appln. Serial No. 2013-524264, dated Jul. 7, 2015 with translation (9 pgs).

Australian Office Action issued in related Australian Patent Appln. Serial No. 2011289158 dated Jun. 19, 2014 (4 pgs).

Mexican Office Action issued in related Mexican Patent Appln. Serial No. MX/a/2013/001744 dated Apr. 10, 2014, with English translation (5 pgs).

PCT International Search Report and the Written Opinion, issued in related application, dated Mar. 16, 2012 (15 pgs).

International Preliminary Report on Patentability issued in related application No. PCT/US2011/047809, dated Feb. 19, 2013 (10 pgs).

Chinese Office Action (w/translation) issued in related application No. 201180049177.5, dated Aug. 19, 2015 (18 pgs).

Mexico Office Action, issued in related Appln. No. MX/a/2013/001744, with English translation; dated Jan. 30, 2014 (6 pgs).

Mexican Official Action issued in related Mexican Patent Appln. Serial No. MX/a/2013/001744, dated Jun. 20, 2014 with translation (5 pgs).

Official Action issued in related U.S. Appl. No. 13/210,333, dated Feb. 10, 2016 (48 pgs).

Official Action issued in related U.S. Appl. No. 13/210,333, dated Mar. 19, 2015 (15 pgs).

Official Action issued in related U.S. Appl. No. 13/210,333, dated Nov. 14, 2014 (15 pgs).

Official Action issued in related U.S. Appl. No. 13/210,333, dated Nov. 1, 2013 (17 pgs).

Official Action issued in related U.S. Appl. No. 13/210,333, dated Jul. 19, 2013 (15 pgs).

Office Action issued in related U.S. Appl. No. 13/210,333 dated Jun. 20, 2017 (63 pages).

Chinese Office Action issued in application No. 201180049177.5, dated Feb. 22, 2017 (25 pgs).

Japanese Office Action (w/translation) issued in application No. 2016-135871, dated May 15, 2017 (9 pgs).

Japanese Office Action issued in application No. 2014-528500, dated Mar. 24, 2017 (14 pgs).

Office Action issued in U.S. Appl. No. 13/210,333, dated Mar. 31, 2017 (62 pgs).

Office Action issued in corresponding European Patent Appln. No. 11817178.4, dated Apr. 18, 2016 (7 pgs).

Japanese Office Action issued in application No. 2014-528500, dated Sep. 15, 2016, with machine English translation (18 pgs).

Chinese Office Action issued in application No. 201180049177.5, dated Jul. 5, 2016 (21 pgs).

Chinese Office Action (no translation) issued in application No. 201180049177.5, dated Mar. 29, 2018 (10 pgs).

European Office Action issued in application No. 12 827 879.3, dated Mar. 8, 2018 (4 pgs).

Japanese Office Action (w/translation) issued in application No. 2016-135871, dated Mar. 28, 2018 (6 pgs).

Office Action issued in U.S. Appl. No. 13/210,333, dated May 14, 2018 (46 pgs).

Canadian Office Action issued in application No. 2,807,949, dated Jul. 17, 2018 (3 pgs).

Chinese Office Action (w/translation) issued in application No. 201180049177.5, dated Sep. 14, 2018 (19 pgs).

* cited by examiner

PORTABLE DRUG DISPENSER

This application claims priority from U.S. application Ser. No. 61/528,225, filed Aug. 27, 2011.

The present invention relates to portable drug dispensing devices, and in particular, portable drug dispensers having one or more chambers for holding one or more drugs, a dispensing mechanism for dispensing the drugs, and a processor for determining the time of activation of the dispensing, mechanism and for optionally determining or recording, measuring other various attributes and variables around dispensing, including attributes of the user (i.e., location, vital signs and body chemistries), and an ability to be communicating with one or more computers remote to the dispenser. The invention has particular utility for determining, monitoring and/or ensuring patient compliance as well as the ability to help modulate and adjust medication timing and dosages, and will be described in connection with such utility, although other utilities are contemplated.

Modern medicine is highly dependent upon medications to prevent, treat and ameliorate diseases and symptoms. Such medications range from nutrients and vitamins, and other supplements, to prophylactic over-the-counter medications (such as aspirin and H2 blockers) to medications for the treatment of diseases (such as hypertension, diabetes and cardiovascular disease).

Many individuals, whether they are seeking to enhance health and wellness via supplements, vitamins or prophylactic medications, as well as patients burdened by acute or chronic disease, take one or more medications in various forms per day.

Compliance to prescribed medication regimens (often termed 'adherence') is often quite low, for example, as low as 50% or lower in many cases. Chronic disease affects ~25% of Americans, yet Americans' compliance, or adherence, is overall often less than 50%. Furthermore, 6 months after being prescribed a new chronic medicine (i.e. for hypertension, high cholesterol) in many cases less than half are being refilled).

This low compliance rates leads to many downsides, including increased disease burden, increased hospitalization rates and billions of additional dollars in care costs, estimated at $180 Billion a year in the US, and leads to over an estimated 20 Million preventable sick days.

In addition, clinical trials, and the safety, efficacy measures required to develop new drugs and combinations often require extensive, rigorous and expensive and phased clinical trials. Assurance that trial subjects are actually taking the test drugs/placebo or other medical components is critical to accurate assessment and the potential success of the trials. Better means of tracking compliance during clinical trials will lead to safer, more effective drugs entering the market.

One of the biggest problems facing society is the trafficking of controlled substances like hydrocodone and oxycodone, which have enormous "street value." Specially packaged, secure cartridges could be hardened and also contain the opioid receptor antagonist Naloxone. Should the cartridge be breeched, the pain medications would be rendered useless by coating them with viscous Naloxone. Moreover, since the portable dispenser can control the frequency with which pain medications are released, the pills could not be immediately dispersed for non-medical or overdose purposes. Furthermore cartridges containing medicines appropriately labeled by electronic, print or other means could be used to validate that contained medications are not counterfeit or otherwise not what was intended. Any information on the cartridge could communicate with a separate or internal database to validate attributes such as manufacturer, drug content, expiration date and validity of the drugs contained within.

Another safeguard to control pain medication usage and assure they are being received only by the intended patient is to incorporate a fingerprint reader, or other means of identifying and individual (voice, face recognition and others) now available incorporated into the device, or linked into electronically linked or tethered smartphones and similar appliances.

In particular with pain medications, the timing and dosing of pain medications (for example Vicodin) highly vary for the patient based on age, genetics, weight and other attributes. A dispenser which can remind the patient of regular dosing intervals to help control pain (for example after a surgery), with optional inputs via the dispenser device to record pain levels, and enable 'as needed/PRN' doses to be delivered would enable a feature similar to hospital based 'Patient Controlled Analgesia' (PCA), in which commonly intravenous pain medications (such as Morphine Sulfate) are delivered at a programmed basal rate (e.g. 5 mg per hour) and the patient can give by push button additional small doses (e.g. 1 mg bolus), to a predetermined maximum within a time window (for example up to 3, 1 mg bolus's per hour). For a personal dispenser containing pain medication, in a similar way, the device could be programmed in various ways (remotely by the clinician, pharmacist or others with appropriate regional licensure) to enable the patient to take regular doses (e.g. every 4 hours 1 Vicodin pill) and to take additional as needed for pain, (for example up to 1 extra Vicodin pill every 30 minutes, not to exceed 3 additional doses in a 6 hour period). The device could include inputs via touch screen or other methods (via smartphone interface for example) to record pain levels and other measures. If pain levels were not adequately controlled the dispenser could be remotely or based on pre-set protocols prescribed by the provider, alter the dosing schedule and PRN settings. Additionally, tapers could be programmed into the dispenser as the patient was being weaned off pain or other medications.

The dispenser could also include incorporation of various sensors which can measure and/or monitor the patient in any number of ways, including but not limited to measurement of heart rate (e.g. using a light/camera source), a camera (which can in a non-contact way measure heartrate), as well as potential attachments or including components which could include but not be limited to a glucometer and other measure of blood lab values such as INR (for blood coagulation) and others. Additional sensors such as accelerometers and/or GPS to track movement/location of the individual carrying the device and location at time of use can be included to help track location and timing of medicine dispensation. Measurement of various attributes and communication to the prescribing clinician, or integration with predetermined or other means of varying dosage, timing and other attributes.

Another issue of medication dispensation is the handling and measuring appropriate doses of liquid medications (most often for children or those who cannot swallow pills). Often medicines, such as Tylenol and Ibuprofin, steroids and antibiotics are dosed from a bottle by inaccurate cup (measuring tablespoons), or by syringe or spoon. This leads to inaccuracies and the likelihood of under or over dosing.

Accurate dosing is particularly critical for more potent medications such as steroids, immunosuppressants (such as cyclosprin) and chemotherapy where dosing and resulting blood levels are critical. Many of these drugs are given outside of the hospital or clinic setting by parents or other caregivers.

A better, more convenient, integrated method is needed, especially for drugs which must be dosed carefully and delivered.

Better means to enhance compliance and record and measure of medications by the individual are needed. This can include 'gamification', for example incentive point rewards or other similar means to help 'reward' the patient in use and compliance with their medications. This can be displayed on the dispenser, connected to mobile phone and various means of display and record. Furthermore the dispensing device could be connected by various means to any number of mobile health "Apps" which integrate compliance tracking, gamification or other means of integrating medication use for any number of conditions.

The present disclosure is directed to devices that overcome the aforesaid and other disadvantages of the prior art. Briefly described, the present disclosure provides a portable drug dispenser that can hold one or a plurality of drug products.

In one aspect, the present disclosure provides a portable drug dispenser which includes a one or more chambers for holding a plurality of separately contained drug products, a dispensing mechanism for dispensing one or more of the plurality of separately contained drugs upon activation of the dispensing mechanism, and a processor configured to determine the time, and potentially other information such as, e.g. location, vital signs, user data input (e.g. pain score) of each activation of the dispensing mechanism, and to transmit the determined time of activation to a computer located remote to the dispenser, optionally stored on the device as well for read out by a clinician managing the patient.

In another aspect, the present disclosure provides a portable drug dispenser which includes a first chamber for holding a plurality of a first type of separately contained drug products, one or more additional chambers for holding a plurality of one or more other types of separately contained drug products, respectively, and a dispensing mechanism for dispensing one or more of the plurality of separately contained drugs upon activation of the dispensing mechanism.

The features, functions, and advantages that have been discussed can be achieved independently in various embodiments of the present disclosure or may be combined in yet other embodiments, further details of which can be seen with reference to the following description and drawings.

Other systems, methods, features, and advantages of the present disclosure such as various other medication cartridge mechanisms for loading the dispensing device could be inserted manually by patient, provider, pharmacist and/or, or by devices with other control mechanisms (i.e. a Pyxis medication type system) or other integrated platform to which the dispenser could be connected, i.e. to integrate possible loading mechanisms for centralized or other forms of medication containers, will be or become apparent to one with skill in the art upon examination of the following drawings and detailed description. It is intended that all such additional systems, methods, features, and advantages be included within this description, be within the scope of the present disclosure, and be protected by the accompanying claims.

Further features and advantages of the invention will be seen from the following detailed description, taken in conjunction with the accompanying drawings, wherein like numerals depict like parts, and wherein.

An appendix is included which shows various potential elements, integration with control mechanisms and applications and example forms of dispensers. These are only examples and do not limit the description or breadth of the described invention and embodiments.

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

Many embodiments of the invention may take the form of computer-executable instructions, including algorithms executed by a programmable computer (contained within or remote (e.g. via cloud based algorithms and computers). Those skilled in the relevant art will appreciate that the invention can be practiced with other computer system configurations as well. Certain aspects of the invention can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices, palm-top computers, implanted and wearable computers, cellular or mobile phones, multi-processor systems, processor-based or programmable consumer electronics, network computers, minicomputers and the like.

The invention can also be practiced in distributed computing environments, where tasks or modules are performed by remote processing devices that are linked through a communications network. Moreover, the invention can be practiced in Internet-based or cloud computing environments, where shared resources, software and information may be provided to computers and other devices on demand. In a distributed computing environment, program modules or subroutines may be located in both local and remote memory storage devices. Aspects of the invention described below may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks. Data structures and transmissions of data particular to aspects of the invention are also encompassed within the scope of the invention. Communication between devices or components provided herein may be accomplished over any wired or wireless network that enables communication between devices, including local area networks (LAN), wide area networks (WAN), the Internet, Wireless LAN, Wi-Fi, mobile device networks, IEEE 802.11, GSM, GPRS, UMTS, WMAN, BWA (LMDS, WiMAX, AIDAAS and HiperMAN), 3G and 4G communications protocols, Bluetooth, or any other network arrangement and/or protocol known to those having ordinary skill in the relevant art. Various standard to advanced means of secure/privacy aspects of data transmission and privacy can be integrated.

The term "drug", as used throughout this disclosure, includes pharmaceutical medicines, nutriceuticals, supplements, vitamins, minerals and the like, in any form.

Also, the term "patient" may include both a human patient, and a non-human animal patient.

Figure 1:
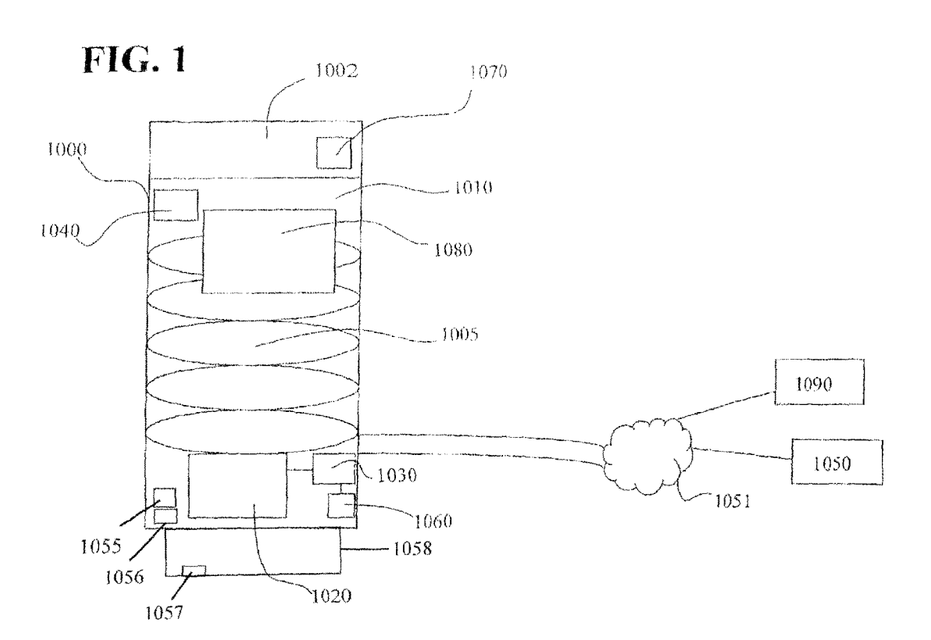
FIG. 1 is an illustration of a block diagram of a portable drug dispenser, in accordance with an embodiment of the present disclosure.

As shown in FIG. 1, a portable drug dispenser 1000 includes a chamber 1010 for holding a plurality of separately contained drug products 1005. The separately contained drug products 1005 may be a combination or compounded drug product, or may be any other drug product. The drug products 1005 may be in any known form, including for example, pill, tablet and capsule forms. The separately contained drug products 1005 may include contained quantities of drugs in powder, liquid, gel, cream and/or solid form, and may contain any drug, including nutriceuticals (for example multivitamins), over-the counter-drugs (for example aspirin) and prescription drugs (for example, but not limited to, blood pressure medications, birth control pills, antibiotics, opiates etc). The drug products 1005 may be loaded directly into the chamber 1010. Alternatively, the drug products 1005 may be loaded into a cartridge 1100 (see FIG. 2) which can be inserted into the chamber 1010. The dispenser 1020 may include a hinged lid 1002, which can be opened before dispensing the drug products 1005.

The dispenser 1000 includes a dispensing mechanism 1020 for dispensing one or more of the drug products 1005. The dispensing mechanism 1020 may include, for example, a spring loaded mechanism which is coupled to a button. When a user pushes the button, the spring is activated and the dispenser 1000 dispenses a single drug 1020 (e.g., from the top of the stack). In another example, the dispensing mechanism 1020 may be coupled to the lid 1002 such that a user may pull on the lid 1020 of the dispenser 1000 to activate the dispensing mechanism 1020 and dispense a drug product 1005. Additional drugs 1005 may be delivered by subsequent activations. In another embodiment, the dispensing mechanism 1020 may include a battery powered motor which may be activated by operating a switch or button on the dispenser 1000. The battery may be replaced manually, or recharged by docking the dispenser 1000 or via power cord or other common means of recharging portable devices (e.g., cell phone, including via cord to USB type cable or others.).

The dispenser 1000 may further include a processor 1030, which may be a programmable processor.

Figure 2:
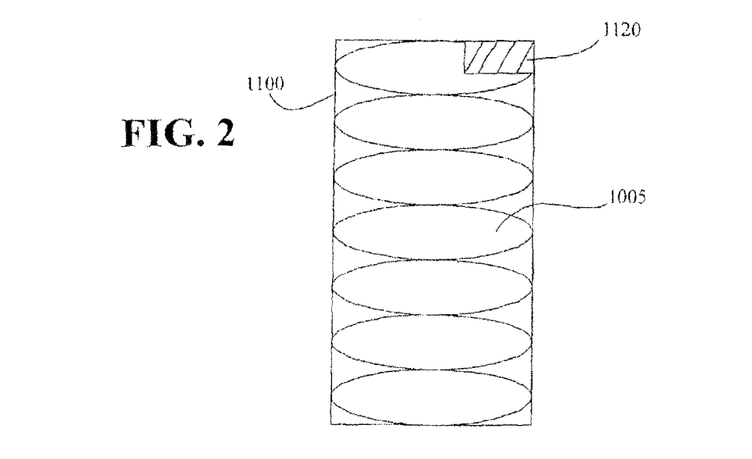
FIG. 2 is an illustration of a block diagram of a cartridge which may be used in a portable drug dispenser, in accordance with an embodiment of the present disclosure.

One or more drug products 1005 can be loaded into the dispenser 1000. For example, the dispenser 1000 may be loaded with daily aspirin, or a multivitamin, or birth control pills. These drugs 1005 could be loaded into the chamber 1010 of the dispenser 1000, into a cartridge 1100 which can be inserted into the chamber 1010 (and which may be optionally removable from the chamber), or other form of holding container in an ordered manner if desired. The end user (e.g., patient or care giver) may place single or multiple (one or more) types of drug products 1005 into the device. In another embodiment the drugs 1005 could be provided in a preloaded cartridge 1100, including blister pack, or other container which could hold meds with any desired type and number. If desired, the cartridge may include a battery so that a fresh battery is installed in the dispenser each time a fresh cartridge is installed.

Example: Individual is taking a blood pressure pill twice a day. The morning pill (Pill A) is different than the evening pill (Pill B). The pills could be loaded into the chamber 1010 of the dispenser 1000, or into a cartridge 1100, or any form that will hold the pills in a desired position. The morning pill would be alternated with the evening pill.

In one example, a week supply of medications (14 pills total, 7 morning and 7 evening pills) may be loaded into the cartridge 1100 (this could be done by a pharmacist, the patient themselves, a caregiver, or be prescribed within this form as alternating pills as a preloaded cartridge). Each cartridge 1100 can be optionally labeled with machine-readable indicia 1120, which may include patient identification, and/or QR or 'bar-code' of various means. May also contain RFID type element by which to be electronically detected.

The dispenser 1000 may further include a scanning element or reader 1040 for 'reading' the machine-readable indicia 1120 on the cartridge. The reader 1040 may communicate with the processor 1030, and through an internal database, or sourced via internet/cloud based database, the processor 1030 may identify the components of the cartridge, including but not limited to indications and instructions for use of each of the one or more drugs, their dose, expiration date, etc. 1005.

The controlled release could be moderated manually, by programmed computer, at the designation based on the patient's vital signs or other measurements (i.e. blood sugar level, blood pressure, mood, pain level, activity level, and others).

Each drug product 1005 dispensed may be recorded, and stored as a record electronically within the dispenser 1000 or transmitted to a remote computer 1050. The dispenser 1000 may transmit information regarding the dispensing of a drug 1005 over a wireless network 1051, or through a wired network, for example, after 'docking' or plugging in of the device to a computer or network (i.e. to a computer via the USB plug). Each time a drug product 1005 is dispensed, the processor 1030 may record the time and location of the dispensing. That is, the processor 1030 may provide a time stamp and location information upon activation of the dispensing mechanism 1020. The dispenser 1000 also may include a sensor 1055 such as a camera 1056 or a saliva detector 1057 carried on a mouthpiece 1058 the dispenser, adapted to detect whether the dispensed drug was dispensed into the patient's hand or mouth, and/or a GPS receiver 1060, or utilize any other known system of location and tracking, to determine the location of the dispenser when a drug 1005 is dispensed.

The device may issue an alert, or otherwise indicate to the user/patient when they are due to take one or more drugs 1005. For example, the dispenser 1000 may include an alert indicator 1070, which may be an audible, visual or physical indicator. For example, the indicator may include a speaker, one or more lights, or a vibrating element. The indicator 1070 may provide the alert by providing an audible sound (e.g., chime, ring, alarm or any other sort of electronic or analog generated sound). The device may issue an alert via a land-line phone ore cellular phone call to the user/patient, also via SMS/Text message, or various means of 'push' alerts via any number of mobile or other applications. The device can communicate with one's family or healthcare provider to document proper adherence to a prescribed medical regimen, as well as prevent direct dispensing to unintended recipients, which is of particular importance for medications with an addictive potential.

The dispenser 1000 may optionally include an integrated screen or display 1080 with which to display patient's variables/vitals, or to integrate and display multiple measurements from the patient, environment or other sources.

The display 1080 may be a 'touch' screen, with multiple touch controls, and may further provide the user with the ability to load in various applications ('Apps') as appropriate to the desires and needs of the clinician, patient and/or caregiver.

Controls can include but are not limited to 'dispense' controls, to 'refill' buttons which will automatically re-order or request refill from pharmacy and/or physician. These controls may be manually operated, or they may be controlled by the processor 1030.

The data obtained by the dispenser 1000 can flow back to the clinician (for example, by providing the data to a computer 1050 to which the clinician may access) who prescribed the drugs as well as to the patient, family, or assigned caregivers and clinicians. A web or otherwise enabled dashboard (including with appropriate security and privacy measures as are state of the art) can display compliance and timings of dosings from the dispenser 1000 over various time windows. A "dashboard" can optionally be displayed on the dispenser.

Data and information can be optionally 'pushed' back by the clinician or other caregiver via the device to optimize, change or cancel various prescriptions. For example, a clinician receiving data indicating a patient's heart rate while on motoprolol given twice a day, noticing relative bradycardia, could indicate via the device/communication to hold evening dosing/dispensing. In another example, a clinician managing a patient's pain, could receive information from the patient on pain levels (communicated via the dispenser or other mechanisms) and alter the timing and dosage of pain meds.

Tracking of adherence/compliance could be leveraged by giving points/badges or other feedback to the individual and optionally integrated with social networks such as FaceBook, or integrated into social gaming, such as those made by Zynga and others. The device could communicate with a mobile phone, for example, to only enable use of 'bonus' features, such as Facebook, or various game type applications, if appropriate medications were taken via the dispenser.

Integration of optional components which measure individual patient metrics also could be integrated into the dispenser. By way of a not limiting example, an accelerometer, which would enable the device to also function as a digital and connected pedometer could be intergrated into the dispenser. It could contain elements related to measuring biophysical measures, for example EKG leads which could measure a patients heart rate and EKG variables (i.e. QT duration . . . a measure effected by some drugs or conditions), which could help determine whether a particular drug would be dispensed on a regular or PRN (as needed) basis. Additional possible integration components could include a glucometer, and other measures of blood biomarkers (e.g. Potassium, and other electrolytes, and other measures commonly obtained by blood sampling).

Improved compliance and responsibility for one's own health leads to better outcomes for chronic disease and prevention. Employer incentive programs are common, and could leverage the dispenser 1000 to track and encourage compliance to prophylactic (i.e. cholesterol lowering agents) and acute to chronic to disease medications. For example, patient compliance data from the dispenser 1000 (such as the time and location of dispensing) can be transmitted from the dispenser 1000 to a computer 1050 accessible to the patient's insurance provider or employer so that the insurance provider or employer can verify the patient's compliance in taking his/her prescribed medications.

Incentives could be, but are not limited to monetary awards, reductions in insurance premiums, or any number of various rewards, prizes or benefits.

The dispenser 1000 may communicate with any computer 1050, which may include any mobile device such as iPhone, Android or other mobile phone/iPod touches and similar via Bluetooth, direct connection (line) or other standard method of device/device or device to network communication. Information can be transmitted both ways, for example: content from the dispenser 1000 may include reports of times of taking pills, number, time stamps, and location (e.g., from GPS integration on the phone or the dispenser 1000). Data can be uploaded via the phone or directly via WiFi, cellular networks or other standard data streams of common use, in secure or unsecure manner to upload information to the dispenser 1000, to include new safety warnings, reminders, updates, schedule changes from the care provider, prescriber or software and feedback algorithms embedded in software based in the cloud, in the patient's and or owners' dispenser 1000, or via their mobile device.

Figure 3:
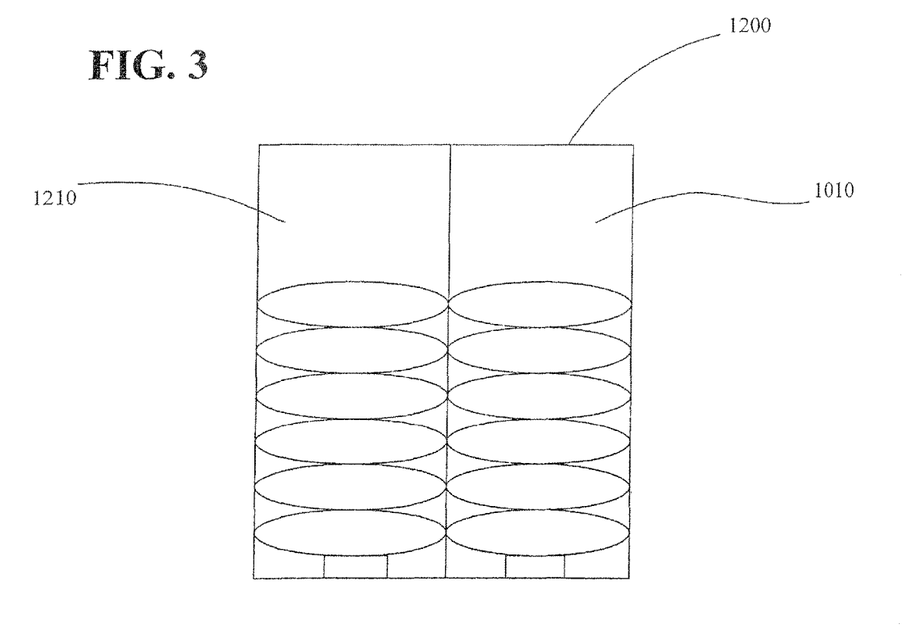
FIG. 3 is an illustration of a block diagram of a portable drug dispenser having two chambers for holding drug products, in accordance with an embodiment of the present disclosure.

The dispenser 1000 may optionally contain two or more types of drug products 1005. For example the primary pill can be a daily aspirin, personalized polypill (or drug combination as provided in co-pending U.S. application Ser. No. 13/210,333, filed Aug. 15, 2011), antibiotic, or other medication taken on a regularly scheduled basis, i.e. for hypertension, diabetes or other disorders, or for prophylactic wellness reasons. Should a 'PRN' as needed dose of pain killer, or for example migraine headache be needed, a second repository of PRN drugs could be accessed to dispense, for example an opiate such as Percocet or Vicodin. As shown in FIG. 3, a dispenser 1100 may include two chambers. A first chamber 1010, as described with respect to FIG. 1 is included, as well as a second chamber 1210. The dispenser 1200 of FIG. 3 may include all of the same elements and functionality as described above with respect to the dispenser 1000 shown in FIG. 1. Three or more chambers also could be included.

The frequency and timing of the PRN meds may be limited and controlled, such that additional extra doses out of desired windows of time and specs (for example one per 2 hour period), will not be allowed. For example, the processor 1030 may count the number of dispensing of a particular drug (e.g., the PRN drug) and, if the number of dispensings of that drug over a predetermined amount of time (e.g., 2 hours) matches or exceeds a predetermined threshold (e.g. one per 2 hours), then the processor will lock and allow the dispensing mechanism 1020 to be activated to dispense that drug until a certain amount of time has lapsed. This would be particularly applicable with drugs which have potential for abuse, such as opiate medications often used to treat pain. As the dispenser could function in a means similar to an intravenous patient controlled analgesia device (PCA) commonly used in the inpatient setting to set an amount of pain medicine that is given intravenously, and with a limited number of bolus doses which can be triggered by the patient. Cartridges of drugs/medications which benefit from tight control (e.g. opiates, certain medications susceptible to abuse and/or addiction or overdose potential) could include 'tamper proof' or tamper resistant cartridges which would render the cartridge and included medications unusable or non-dispensable if the cartridge was breached/opened in any way not mediated or tracked by the dispenser.

Drugs 1005 may be pre-configured into 'cartridges' 1100 that would fit in the dispenser 1000. Morning, Afternoon and Evening pills could be placed in appropriate order for example, or just AM, and PM dosings. Additionally a personalized polypill (or any combination or compounded drug) with multiple of a patient's medications integrated into a single tablet, could be manufactured and put into cartridge form, following the teachings of my co-pending U.S. application Ser. No. 13/210,333, filed Aug. 15, 2011. Thus, a variety of pill sizes and shapes could be contained within the dispenser 1000. In one embodiment, more than one pill type could be dispensed, for example a dispenser 1000 which contained pills for blood pressure, diabetes, and migraine headaches. The first two (blood pressure and diabetes) would be dispensed on a regular set schedule (or one altered based on the patients real-time measured data), and the as needed migraine treatment pills would only be dispensed via the dispenser 1000 on a PRN basis. The PRN meds could be controlled and limited by lock-outs and dosing limits (which may be controlled by the processor 1030), similar to PCA devices for pain control used commonly which enable programming of doses, timings, lockouts, total doses within a time period.

Other utilities are possible. For example, pharmaceutical companies and contract research agencies around the world conduct lengthy and expensive clinical trials on new drugs, combinations, dosings and indications. A key component of trials is assurance that the drugs (or placebo or alternative treatment/drug arms) were actually taken. Using the dispenser 1000, the taking of the medicine, time stamped, and verified could be recorded and transmitted in a variety of ways via the dispenser 1000 to those running and analyzing any drug trial. The dispenser 1000 can additionally include a voice recorder for the trial participant to note and record any side effects, symptoms (good and bad) or other notations. The dispenser 1000 can additionally include a touch screen for the trial participant to note and record any side effects, symptoms (good and bad) or other notations. The dispenser can record and integrate various physiologic or other measures, including but not limited to physiology data (e.g. from a heart rate monitor, pedometer, glucometer, urine, blood or other fluid analysis). As described in co-pending U.S. application Ser. No. 13/210,333, filed Aug. 15, 2011 the dispenser and included or remotely accessed computer could integrate various information and data relevant to the individual to inform drug dose, combination, timing and other modifications, optimizations and changes of treatment regimen. An example could include blood pressure medications. Blood pressure values could be recorded from an integrated finger blood pressure cuff, or external device, and as trends and BP values are determined, pre-set algorithms could inform the dispense to deliver or 'hold/skip' a dose of antihypertensive. For example a patients blood pressure is running low, and the dispenser 'holds' the evening dose.

In the context of a clinical trial or everyday use, a visible, and or auditory alarm, and or vibratory alarm as well transmission of reminder information via cell phone, pager, website or other modality as optional display can remind the patient or caregiver when it's time to take their medications.

In a further embodiment, the contained drug products 1005 may be marked with edible RFID like or other identifying trackable chips (such as the 'raisin' technology developed by Proteus Biomedical, Inc., of Redwood City, Calif.), and as described, for example in U.S. Published Application Serial No. 2008/0284599A.

The dispenser 1000 can also optionally read each pill through the reader 1040, which may include optical or other means, if each pill has any marker ranging from RFID or other embedded information, to use of camera or reader of many varieties to read and record a barcode, QR code, actual text, color or other attributes of each pill. In this way a very detailed record of each dispensed pill could be recorded for use in compliance, clinical trials, self reporting for the patient, and could augment safety and timing of each pill/medicine dispensed. Additionally the dispenser 1000 can contain a camera which can take a picture, and optionally store and transmit of dispensed medications.

The dispenser 1000 may communicate to the patient by sound (e.g., different beeps or alarm sounds or buzz patterns can indicate different medications and timings, or even recorded messages such as 'time to take your medication now . . . please place top in your mouth and hit the 'dispense' button").

An LCD or other type of common screen or display 1080 (e.g., as used in PDA's phones, digital watches etc) can display information to the user, and also include inputs, such as ways to set the scheduling of drugs/pills contained within.

The dispenser 1000 may be programmed directly via the screen via touch based user interface or with one or more buttons (similar to how a digital watch or timer or many other electronic devices are programmed, such as one button to control menu and an additional button(s) to set time, date windows etc.

Voice interface to optionally include voice recognition (run by software in onboard computer, or via cell phone or via the web or other networked interface) could program the dispenser 1000 as well to set timings of alarms and other features such as to record treatment or side effects.

The dispenser 1000 may contain a small onboard battery powered computer (e.g., the processor 1030) which would also potentially be linked to data inputs and would help determine when/if dosings for the patient.

Data inputs from the user could include vital signs (e.g., as measured by external measurement devices 1090, which may include wearable devices on the patient that measure heart rate, blood pressure, and/or activity, and may further include optional built in accelerometer or data derived from sensors in the users mobile phone or other networked device which communicates with the dispenser 1000).

As an example, the user may be a diabetic patient, and sensors on the user could detect blood sugar levels and trigger the patient to take a glycemic medicine (like glyburide or metformin) if blood sugars reach a certain preset threshold. Or, similarly, a patient with hypertension could be alerted to take their medication in the dispenser 1000 should their blood pressure reach a certain measure, or actually have their medication held (i.e. device would not dispense or alarm the patient to take) if blood pressure readings were in normal or low range.

In accordance with the present invention, there are many applications for detecting patient data and utilizing this data to interact with the dispenser 1000 to alter based on pre-scribed algorithms and guidelines from a prescriber (doctor, etc), in which to help optimize if and when a medicine was to be dispensed.

Creation of 'designer' or personalized meds/pills/drug products 1005 which contain multiple medications specific for a user (compounded medicine), and individual 'polypills' or combination drug products (e.g., individually made pills containing 2 or more medicines prescribed for the individual) are described in my aforesaid U.S. application Ser. No. 13/210,333, filed Aug. 15, 2011, the contents which are incorporated herein by reference. Such drug products can also be printed with patient's name, a bar code, QR code or other identifying markings. Further, such combination or compound drug products may be designed to be manufactured into pills/capsules which specifically fit the dispenser 1000. The dispenser 1000 may record their use as described, or simply contain and manually dispense.

In one embodiment, the personalized pills or combination drugs could be 'printed' or added to a cartridge 1100 that is designed to fit within the dispenser 1000. 'Morning' and 'Evening' pills could be alternated such that with each dispensement the AM/PM pills would be dispensed alternatively.

The dispenser 1000 may further include a button or other activation mechanism (both manual and potentially automatic or programmatic based on low levels of drug) which may be activated to order refills of contained meds. Furthermore, the processor 1030 may be configured to count or otherwise determine how full the chamber 1010 or cartridge 1100 is, and alert the user to order a refill when the chamber 1010 or cartridge 1100 is low. Alternatively, or additionally, the processor 1030 may transmit a signal to a computer located at a pharmacy or a clinician's office to automatically order a refill.

In another embodiment, the dispenser 1000 may include an emergency button, to signal/call/alert care provider(s) (ranging from doctor, EMS/911, friends and family etc). This could alert via integrated communication via cell phone and/or the internet (Bluetooth or WiFi enabled device), and could also communicate the patient/user's position (via GPS or other marker of location). In another embodiment, the dispenser may include measurements from a built in accelerometer, programmed to function as a 'fall detector', and enable automated activation of signal/call/alert should the user had a fall. Together with a built in GPS or other component to identify location this information could be utilized in alert notification to family, EMS/911, call centers and others.

Additionally, the dispenser 1000 may include a patient authorization element, which may be any known element for authorizing a user, including for example, a fingerprint reader, voice recognition element, face recognition, retinal detection or facial recognition via an integrated camera, or keypad code.

In another embodiment relates to a means to enhance detection and assurance of compliance and tracking of medicine dispensing that leads to actual ingestion by the patient/user—in this embodiment the action of dispensing a pill into a presenting mouthpiece requires the patient to moisten his/her lips, creating a low-current continuity path to both release the pill and record the action. A lithium coin battery or similar power source, including an option from an attached mobile phone or similar appliance, would drive this simple circuit. An alternate embodiment would be to incorporate the detection of saliva by various means, such as detection of salivary amylase or similar marker, possibly with a proteomic chip integrated into the mouthpiece.

In an embodiment to help prevent misappropriation of narcotic substances or other pills, pills could be coated with a colored film (for example, cellulose) that would quickly change color (or blanche) if it was removed from the cartridge in any means other than dispenser control, for example if a pill came in contact with saliva. It would be then easy to visually detect if pills had been inappropriately extracted from a dispenser for resale. The dispenser could communicate to physician/prescriber/family members or others by various means if there was indication that that device was 'tampered' with i.e. the cartridge or dispenser was breached, and/or medications were dispensed to those not indicated.

In one embodiment, the dispenser could also issue preset or adjustable and prescribed unit volumes (as designated by the user/patient or prescriber) of medication drug or supplement in liquid or gel form (as often the case in pediatrics, oral formulations may only be available in liquid or gel or cream form). Adjusted volume/dosage could be modulated directly via inputs on the dispenser or optionally remotely, as indicated by various parameters.

In a further embodiment, drugs in a cartridge format similar to those of coffee cartridge used commonly for dispensing various coffee and tea (for example by the company Keurig)—could contain the daily medications of an individual. The drugs dispensed could be dependant on the attributes and needs of the patient at the time of dispensation, including aspects such weight, blood pressure, blood sugar, INR and other factors. For example if a patient had gained fluid weight and was on a diuretic such as lasix, and the cartridge contained 2 10 mg doses of Lasix. If the patients weight was higher than desired an extra pill (more than the standard 10 mg dose) could be dispensed. Similarly various Coumadin doses (from 1 mg pills in the cartridge) could be dispensed), and adjusted based on the degree of anticoagulation needed as measured by blood (INR) levels or other methods.

Further details and embodiments of the invention are seen in Appendix A, the contents of which are incorporated herein by reference.

Various changes may be made in the invention without departing from the spirit and the scope thereof. It should be emphasized that the above-described embodiments of the present portable drug dispenser are merely possible examples of implementations and are merely set forth for a clear understanding of the principles of the invention. Many different embodiments of the portable drug dispensers described herein may be designed and/or fabricated without departing from the spirit and scope of the invention. All these and other such modifications and variations are intended to be included herein within the scope of this disclosure and protected by the following claims. Therefore the scope of the invention is not intended to be limited except as indicated in the appended claims.

What is claimed is:

1. A portable drug dispenser, comprising:
   a chamber for holding a plurality of separately contained drug products;
   a dispensing mechanism for dispensing one or more of said plurality of separately contained drugs upon activation of the dispensing mechanism by a patient or caregiver;
   a processor configured to determine the time of each activation of the dispensing mechanism, and to transmit the determined time of activation to a computer located remote to the dispenser; and
   a sensor in the form of a saliva detector carried on the dispenser and adapted to detect whether the dispensed drug was dispensed into the patient's mouth, wherein the processor is also configured to transmit information from said dispenser to the computer located remote to the dispenser, wherein the dispenser (1) is sized to be hand held, and (2) is adapted to be activated by the patient or caregiver.

2. The drug dispenser of claim 1 further characterized by one or more of the following features:
   (a) wherein the processor is further configured to receive information relating to a particular patient for whom the drug products are for treating, and to control the activation of the dispensing mechanism based on said received information, wherein said information is received from one or more measurement devices for measuring an indicator of patient health;
(b) wherein the processor is further configured to determine the location of the dispenser at the time of each activation of the dispensing mechanism, and to transmit the determined time and location of activation to a computer located remote to the dispenser, wherein the processor determines the location of the dispenser based on information received from a GPS receiver;
(c) wherein the processor is further configured to alert a patient or caregiver to activate the dispensing mechanism, in the form of an audible alert, a visual alert, or a vibratory;
(d) further comprising a display;
(e) wherein the processor is further configured to determine a level of fullness of the dispenser, and to transmit to a pharmacy a request to refill a prescription when the processor has determined that the level of fullness of the dispenser or a cartridge within the dispenser is below a predetermined threshold value; and
further comprising a patient or caregiver authentication element for authenticating the patient or caregiver, wherein said authentication element is configured to communicate with the processor and the processor is configured to allow the dispensing mechanism to be activated only after the patient or caregiver has been authenticated.

3. The drug dispenser of claim 1, wherein said chamber is configured to hold a cartridge that is loaded with the plurality of separately contained drug products.

4. The drug dispenser of claim 3, further characterized by one or more of the following features:
(a) wherein the processor is further configured to receive information relating to a particular patient for whom the drug products are intended for treating, and to control the activation of the dispensing mechanism based on said received information, wherein said information is received from one or more measurement devices for measuring an indicator of patient health;
(b) wherein the processor is further configured to determine the location of the dispenser at the time of each activation of the dispensing mechanism, and to transmit the determined time and location of activation to a computer located remote to the dispenser;
(c) wherein the processor is further configured to alert a patient or caregiver to activate the dispensing mechanism, in the form of an audible alert, a visual alert, or a vibratory alert;
(d) further comprising a display;
(e) wherein the processor is further configured to determine a level of fullness of the dispenser, and to transmit to a pharmacy a request to refill a prescription when the processor has determined that the level of fullness of the dispenser or a cartridge within the dispenser is below a predetermined threshold value; and
(f) further comprising a patient or caregiver authentication element for authenticating the patient or caregiver, wherein said authentication element is configured to communicate with the processor and the processor is configured to allow the dispensing mechanism to be activated only after the patient or caregiver has been authenticated.

5. The drug dispenser of claim 1, wherein the drug products comprise liquid medications.

6. The drug dispenser of claim 5, wherein the liquid medications are contained in discrete elements of set liquid volume.

7. The portable drug dispenser of claim 1:
wherein the chamber for holding a plurality of separately contained drugs comprises a first chamber for holding a plurality of a first type of separately contained drug products; and a second chamber for holding a plurality of a second type of separately contained drug products;
wherein the dispensing mechanism is adapted for dispensing one or more of said plurality of separately contained drugs from the first chamber or the second chamber, upon activation of the dispensing mechanism.

8. The drug dispenser of claim 7, further comprising a display.

9. The drug dispenser of claim 7, wherein the processor determines the location of the dispenser based on information received from a GPS receiver.

10. The drug dispenser of claim 7, wherein the processor is further configured to receive information relating to a particular patient for whom the drug products are intended for treating, and to control the activation of the dispensing mechanism based on said received information, wherein said information is received from one or more measurement devices for measuring an indicator of the patient's health.

11. The drug dispenser of claim 10, wherein the processor is further configured to alert a patient or caregiver to activate the dispensing mechanism, wherein the alert comprises at least one of an audible alert, a visual alert and a vibratory alert.

12. The drug dispenser of claim 10, further comprising a patient or caregiver authentication element for authenticating a patient or caregiver, wherein said authentication element is configured to communicate with the processor and the processor is configured to allow the dispensing mechanism to be activated only after the patient or caregiver has been authenticated, wherein the authentication element comprises at least one of a fingerprint reader, facial recognition, a voice recognition device, and a sequence of keypad entries.

13. The drug dispenser of claim 10, wherein said processor is configured to determine the number of times that one of the first type or second type of drug products have been dispensed over a predetermined period of time, and to prevent further dispensing of said one of the first type or second type of drug products if said number of times that the respective one of said first type or second type of drug products have been dispensed over a predetermined period of time exceeds a predetermined threshold value.

14. The drug dispenser of claim 7, wherein said first chamber is configured to hold a first cartridge that is loaded with the plurality of the first type of separately contained drug products, and the second chamber is configured to hold a second cartridge that is loaded with the plurality of the second type of separately contained drug products.

15. The drug dispenser of claim 14, wherein said first and second cartridges include machine-readable indicia for identifying the type of drug product contained within the cartridges, and wherein said dispenser further comprises a reader for reading said indicia.

16. The drug dispenser of claim 15, wherein said machine-readable indicia further identifies a particular patient for whom the drug products are intended for treating.

17. A portable drug dispenser, comprising:
a chamber for holding a plurality of separately contained drug products;

a dispensing mechanism for dispensing one or more of said plurality of separately contained drugs upon activation of the dispensing mechanism by a patient or caregiver;

a processor configured to determine the time of each activation of the dispensing mechanism, and to transmit the determined time of activation to a computer located remote to the dispenser; and a sensor in the form of a saliva detector carried on the dispenser and adapted to detect whether the dispensed drug was dispensed into the patient's mouth, wherein the saliva detector comprises a continuity path detector or a proteomic chip detector integrated into a mouthpiece of the dispenser, and wherein the processor is also configured to transmit information from said sensor to the computer located remote to the dispenser, wherein the dispenser is sized to be hand held and is adapted to be activated by the patient or caregiver.

* * * * *